(12) United States Patent
Tait

(10) Patent No.: US 9,173,709 B2
(45) Date of Patent: *Nov. 3, 2015

(54) PENIS EXTENDER

(71) Applicant: Kevin Tait, Austin, TX (US)

(72) Inventor: Kevin Tait, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/530,865

(22) Filed: Nov. 3, 2014

(65) Prior Publication Data

US 2015/0051445 A1     Feb. 19, 2015

Related U.S. Application Data

(63) Continuation of application No. 13/748,688, filed on Jan. 24, 2013, now Pat. No. 8,905,917.

(51) Int. Cl.
*A61F 5/00* (2006.01)
*A61B 19/00* (2006.01)
*A61F 5/41* (2006.01)

(52) U.S. Cl.
CPC .. *A61B 19/00* (2013.01); *A61F 5/41* (2013.01)

(58) Field of Classification Search
CPC .................................. A61F 5/41; A61B 19/00

USPC ................................ 600/38–41; 128/897–898
See application file for complete search history.

(56) References Cited

U.S. PATENT DOCUMENTS

| | | | |
|---|---|---|---|
| 5,707,341 A | 1/1998 | Mathewuse | |
| 5,836,864 A | 11/1998 | Clark, Jr. | |
| 6,416,460 B1 | 7/2002 | Jochum | |
| 8,162,819 B2 | 4/2012 | Adams | |
| 8,905,917 B2 * | 12/2014 | Tait | 600/38 |
| 2007/0093687 A1 | 4/2007 | Hoefer | |
| 2008/0276944 A1 | 11/2008 | Cvetanovic | |
| 2009/0318754 A1 | 12/2009 | Ettmer | |
| 2010/0016656 A1 | 1/2010 | Rudi | |
| 2013/0018221 A1 | 1/2013 | Ball | |

* cited by examiner

*Primary Examiner* — John Lacyk
(74) *Attorney, Agent, or Firm* — Pierson IP, PLLC

(57) ABSTRACT

A system for extending a penis. The system includes a woven cylinder. The woven cylinder includes a set of fibers woven into a cylindrical shape. The woven cylinder is configured to lengthen when a force is applied to the woven cylinder and decrease in circumference when the woven cylinder lengthens. The woven cylinder is further configured to be placed on the penis of a user, applying a lateral force to the penis.

14 Claims, 2 Drawing Sheets

PENIS EXTENDER

CROSS-REFERENCE TO RELATED APPLICATIONS

This application is a continuation of U.S. patent application Ser. No. 13/748,688, filed Jan. 24, 2013, which is hereby incorporated by reference in its entirety.

BACKGROUND OF THE INVENTION

Penis enlargement, sometimes euphemistically called male enhancement, are techniques alleged to increase the girth, length, or hardness of the human penis. Procedures range from manual exercises to stretching devices and surgical procedures, with reports of successes and failures around the world. While some of these are known to be outright hoaxes, other techniques, such as surgery, can produce some measure of success.

Little legitimate scientific research has been done specifically on penile enlargement, so any claims of significant and permanent enlargement tends to be anecdotal. There are also risks inherent to some of the more invasive procedures, with negative outcomes ranging from the tearing of skin and scarring, to permanent loss of sexual function. Due to the speculative nature of any hope for "improvement" and the many known cases of permanent injury involved in this endeavor, many medical professionals are skeptical of the subject.

At present, there is no proof of any non-surgical technique that permanently increases either the thickness or length of a normal penis. However, many of the techniques are meant only to temporarily lengthen the penis, even under optimal conditions. For example, drugs that promise to lengthen a penis increase are intended to increase the blood flow to the penis. However, this does not physiologically change the penis size.

Accordingly, there is a need in the art for a device which can permanently extend the length of a penis. Further, there is a need in the art for the device to do so without surgery.

BRIEF SUMMARY OF SOME EXAMPLE EMBODIMENTS

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

One example embodiment includes a system for extending a penis. The system includes a woven cylinder. The woven cylinder includes a set of fibers woven into a cylindrical shape. The woven cylinder is configured to lengthen when a force is applied to the woven cylinder and decrease in circumference when the woven cylinder lengthens. The woven cylinder is further configured to be placed on the penis of a user, applying a lateral force to the penis.

Another example embodiment includes a system for extending a penis. The system includes a woven cylinder. The woven cylinder includes a set of fibers woven into a cylindrical shape. The woven cylinder is configured to lengthen when a force is applied to the woven cylinder and decrease in circumference when the woven cylinder lengthens. The woven cylinder is further configured to be placed on the penis of a user, applying a lateral force to the penis. The system also includes an elastic material. The elastic material is configured to provide a force on the woven cylinder.

Another example embodiment includes a method for extending a penis of a user. The method includes placing a woven cylinder over the penis of a user. The woven cylinder includes a set of fibers woven into a cylindrical shape. The woven cylinder is configured to lengthen when a force is applied to the woven cylinder and decrease in circumference when the woven cylinder lengthens. The woven cylinder is further configured to be placed on the penis of a user, applying a lateral force to the penis. The woven cylinder is attached to an elastic material. The elastic material is configured to provide a force on the woven cylinder. The method also includes providing a force on the elastic material.

These and other objects and features of the present invention will become more fully apparent from the following description and appended claims, or may be learned by the practice of the invention as set forth hereinafter.

BRIEF DESCRIPTION OF THE DRAWINGS

To further clarify various aspects of some example embodiments of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF SOME EXAMPLE EMBODIMENTS

Reference will now be made to the figures wherein like structures will be provided with like reference designations. It is understood that the figures are diagrammatic and schematic representations of some embodiments of the invention, and are not limiting of the present invention, nor are they necessarily drawn to scale.

Figure 1:
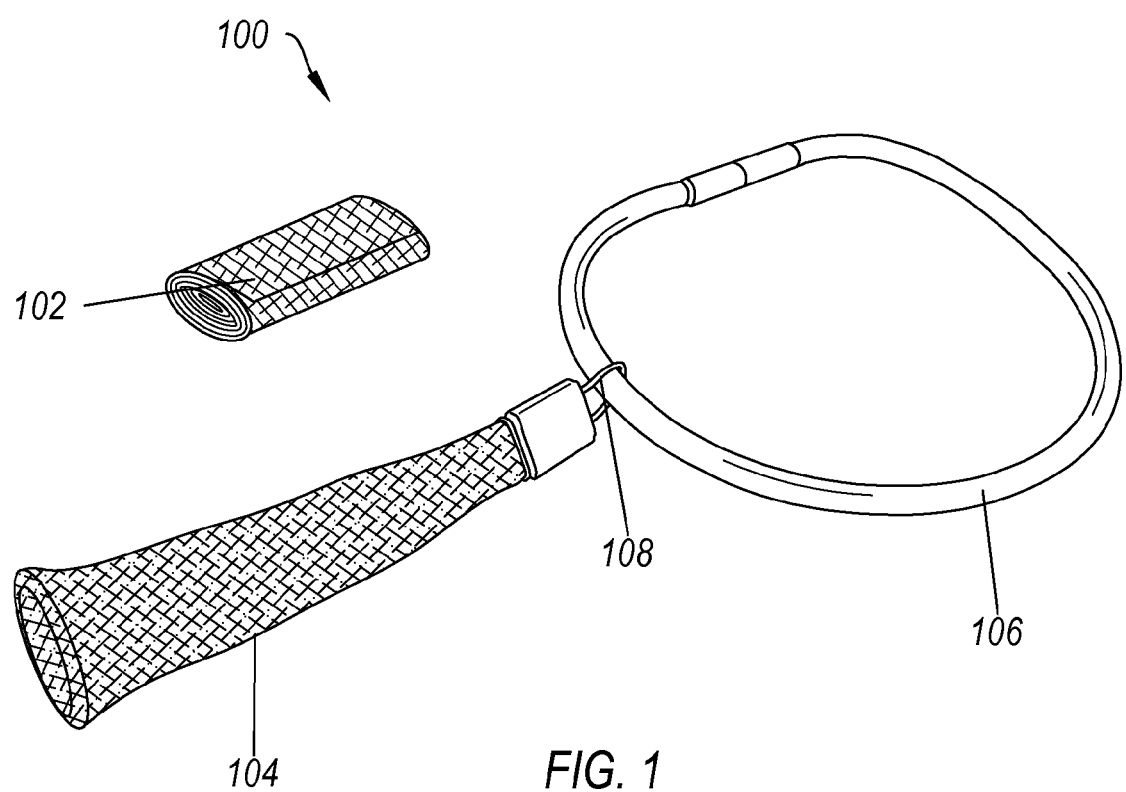
FIG. 1 illustrates an example of a penis extender.

FIG. 1 illustrates an example of a penis extender 100. The penis extender 100 can stretch the ligaments in a penis, causing the penis to stretch and become larger. In particular, the penis extender is configured to provide a lateral force on the penis, stretching the ligaments inside the penis.

FIG. 1 shows that the penis extender 100 can include a wrap 102. The wrap 102 can be placed around the penis of the user to protect the penis during use. I.e., the wrap can prevent the penis extender 100 for abrading or otherwise damaging the penis of the user. Additionally or alternatively, the wrap 102 can assist in helping to extend the penis of the user. For example, the wrap 102 can include a compression wrap or other bandage.

FIG. 1 also shows that the penis extender 100 can include a woven cylinder 104. The woven cylinder 104 can be configured to be placed over the penis of the user. As force is applied to the woven cylinder 104, the circumference of the woven cylinder 104 decreases, securing the penis of the user. For example, the woven cylinder can include a biaxial braid (i.e., a braided structure with two yarn systems one running in one direction and the other in the opposite direction). The tightening is simply a normal behavior of a cylindrical, helically wound braid. Pulling the entire braid lengthens and narrows it. The length is gained by reducing the angle between the warp and weft threads at their crossing points, but this reduces the radial distance between opposing sides and hence the overall circumference. The more force applied to the woven cylinder 104, the more the circumference shrinks. The woven cylinder 104 can be made of any desired material. For example, the woven cylinder 104 can include nylon, cotton or any other desired material.

FIG. 1 further shows that the penis extender 100 can include an elastic material 106. The elastic material 106 can be configured to provide a force on the woven cylinder 104. I.e., the elastic material 106 can be secured to an external device or force can be applied to the elastic material 106. The force is then transmitted to the woven cylinder 104 where it is applied to the penis. The elastic material 106 can include any desired material which rebounds under pressure. For example, the elastic material 106 can include an elastomer, rubber or any other elastic material. The elastic material 106 can include any desired shape. For example, the elastic material 106 can be in the shape of a torus. E.g., the elastic material 106 can include a loop of elastomer with a disc-shaped cross-section.

FIG. 1 additionally shows that the penis extender 100 can include an attachment 108. The attachment 108 can be configured to transfer force from the elastic material 106 to the woven cylinder 104. Additionally or alternatively, the attachment 108 can allow the woven cylinder 104 to move relative to the elastic material 106. This can allow the user to provide force to the elastic material 106 to a variety of points, depending on the location or preference of the user. For example, the attachment 108 can include a cord, such as a string or thread.

Figure 2:
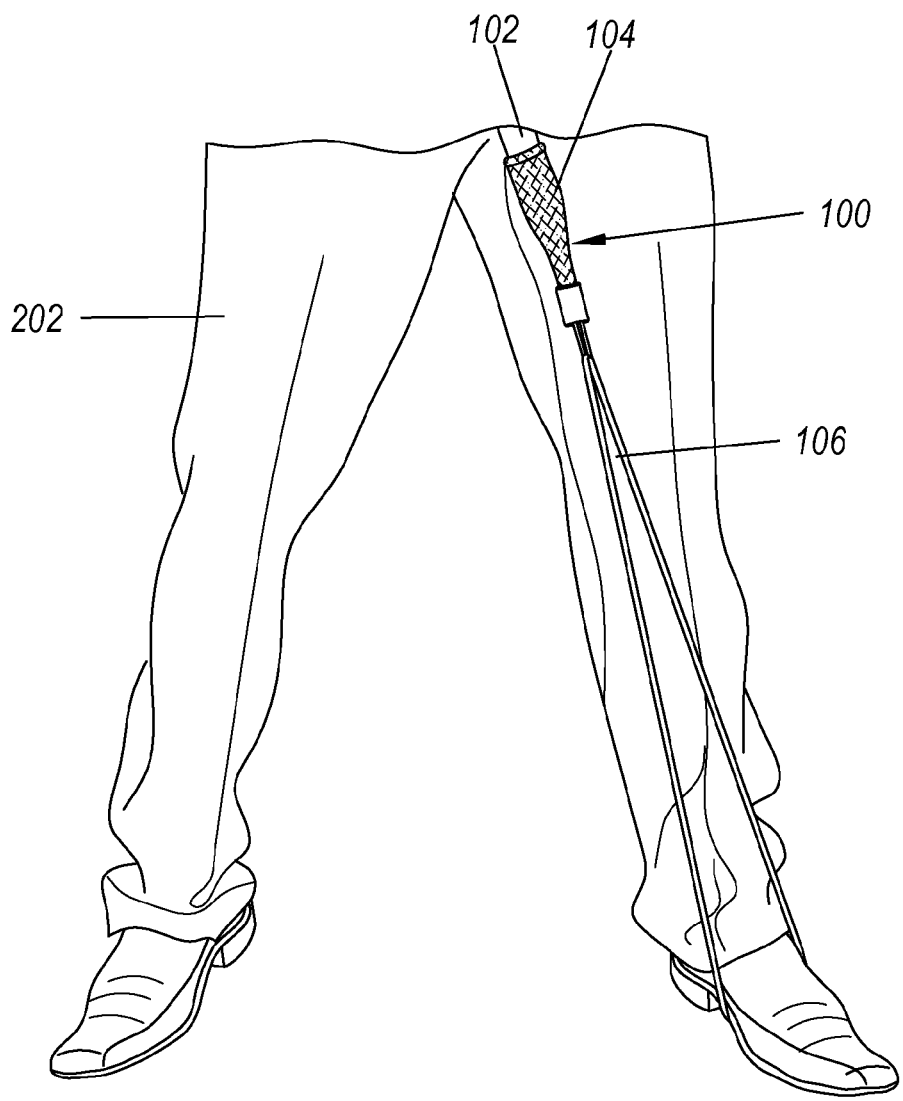
FIG. 2 illustrates an example of a penis extender in use.

FIG. 2 illustrates an example of a penis extender 100 in use. In use, the force applied to the penis of the user via the woven cylinder 104 can lengthen the penis of the user. I.e., the force can stretch the ligaments to make the penis longer. In particular, the penis extender 100 can increase both the penis length and girth by using traction, from its elastic material 106, to assist the body's natural ability to change and develop under physical influence. I.e., if the penis is subjected to constant stretching the cells will begin to divide and multiply, thus increasing tissue mass.

FIG. 2 shows that the wrap 102 is placed over the penis of the user 202. The woven cylinder 104 is then placed around the wrap 102. Force is applied to the woven cylinder 104, reducing to the circumference until the hoop stress applied to the penis of the user 202 is sufficient to secure the penis of the user 202. I.e., the circumference of woven cylinder 104 reduces to the point that the circumference will no longer reduce and lateral force is applied to the penis of the user 202. The elastic material 106 is then secured to an external device, the foot of the user 202 in FIG. 2; however, one of skill in the art will appreciate that the elastic material 106 can be attached to any desired external device.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A system comprising:
a penis extender including a first end and a second end, the first end being configured to be placed on a penis of a user, and the second end being configured to receive an external force, wherein a length and a circumference of the penis extender is configured to change responsive to the second end receiving the external force;
an external member being coupled to the second end of the penis extender, wherein the external member is configured to apply the external force; and
a wrap being configured to be positioned between the penis of the user and the penis extender, wherein a first end of the wrap is configured to be positioned between the first end of the penis extender and the second end of the penis extender, and a second end of the wrap is configured to be positioned outside of the penis extender.

2. The system of claim 1, wherein the penis extender includes a set of woven fibers, and the first end is an open end.

3. The system of claim 1, wherein the external force is received in a direction in parallel to the length of the penis extender.

4. The system of claim 1, wherein the wrap is a compression wrap.

5. The system of claim 1, wherein the length of the penis extender is configured to increase responsive to the external force pulling the second end of the penis extender, and the circumference of the penis extender is configured to decrease responsive to the external force pulling the second end of the penis extender.

6. The system of claim 1, wherein the length of the penis extender is configured to decrease responsive to the external force pushing the second end of the penis extender, and the circumference of the penis extender is configured to increase responsive to the external force pushing the second end of the penis extender.

7. The system of claim 1, wherein the external force is a linear force.

8. A method comprising:
positioning a first end of a penis extender over a first end of a penis extender;
applying external force to a second end of the penis extender;
coupling an external member to the second end of the penis extender;
applying the force, via the external member, to the penis extender;
positioning a wrap being between the penis of the user and the penis extender, wherein a first end of the wrap is configured to be positioned between the first end of the penis extender and the second end of the penis extender, and a second end of the wrap is configured to be positioned outside of the penis extender; and
changing a length and a circumference of the penis extender responsive to the second end of the penis extender receiving the external force from the external member.

9. The method of claim 8, wherein the penis extender includes a set of woven fibers, and the first end is an open end.

10. The method of claim 8, further comprising:
receiving, by the penis extender, the external force in a direction in parallel to the length of the penis extender.

11. The method of claim 1, wherein the wrap is a compression wrap.

12. The method of claim 8, further comprising:
increasing the length of the penis extender responsive to the external force pulling the second end of the penis extender; and
decreasing the circumference of the penis extender responsive to the external force pulling the second end of the penis extender.

13. The method of claim 8, further comprising:
decreasing the length of the penis extender responsive to the external force pushing the second end of the penis extender; and increasing the circumference of the penis extender responsive to the external force pushing the second end of the penis extender.

14. The method of claim 8, wherein the external force is a linear force.

* * * * *